(12) United States Patent
Klose et al.

(10) Patent No.: US 8,783,122 B2
(45) Date of Patent: Jul. 22, 2014

(54) MOVEMENT SENSOR AND SYSTEM FOR ESTABLISHING A MOVEMENT PROFILE

(75) Inventors: Hans-Peter Klose, Stuttgart (DE); Thorsten Sohnke, Asperg (DE); Thomas Wittig, Ehningen (DE)

(73) Assignee: Robert Bosch GmbH, Stuttgart (DE)

( * ) Notice: Subject to any disclaimer, the term of this patent is extended or adjusted under 35 U.S.C. 154(b) by 114 days.

(21) Appl. No.: 13/322,079

(22) PCT Filed: May 4, 2010

(86) PCT No.: PCT/EP2010/056008
§ 371 (c)(1),
(2), (4) Date: Feb. 1, 2012

(87) PCT Pub. No.: WO2011/000610
PCT Pub. Date: Jan. 6, 2011

(65) Prior Publication Data
US 2012/0118084 A1 May 17, 2012

(30) Foreign Application Priority Data
Jul. 1, 2009 (DE) .......................... 10 2009 027 365

(51) Int. Cl.
*A61B 5/00* (2006.01)

(52) U.S. Cl.
USPC .......................................................... 73/865.4

(58) Field of Classification Search
None
See application file for complete search history.

(56) References Cited

U.S. PATENT DOCUMENTS

| | | | |
|---|---|---|---|
| 8,185,191 B1 * | 5/2012 | Shapiro et al. ................ | 600/521 |
| 2003/0065257 A1 | 4/2003 | Mault et al. | |
| 2008/0214360 A1 | 9/2008 | Stirling et al. | |
| 2010/0256531 A1 * | 10/2010 | Nishibayashi ............... | 600/595 |
| 2010/0280578 A1 * | 11/2010 | Skelton et al. ................. | 607/62 |

FOREIGN PATENT DOCUMENTS

WO   WO 2009/013708   1/2009

OTHER PUBLICATIONS

International Search Report, PCT International Application No. PCT/EP2010/056008, dated Jul. 9, 2010.

* cited by examiner

*Primary Examiner* — Robert R Raevis
(74) *Attorney, Agent, or Firm* — Kenyon & Kenyon LLP

(57) ABSTRACT

A movement sensor for establishing a movement profile of a living being, in particular a human, is characterized in that the movement sensor has an arrangement for automatically changing between various operating modes.

11 Claims, 2 Drawing Sheets

MOVEMENT SENSOR AND SYSTEM FOR ESTABLISHING A MOVEMENT PROFILE

FIELD OF THE INVENTION

The present invention relates to a movement sensor and a system for establishing a movement profile of a living being, in particular a human, and the use of a movement sensor for establishing a movement profile.

BACKGROUND INFORMATION

Devices for detecting movements or physical activity have been available for some time from the field of sports. For example, watches are used, which allow the pulse to be monitored. A movement sensor in a shoe allows detection of the cadence during cycling. Comparable sensors are also available in the field of medicine, with the aid of which a movement or activity profile of the patient may be established. Such movement profiles may be helpful within the scope of a diagnosis or therapy, e.g., in the case of overweight patients or during rehabilitation measures.

It is often necessary to establish a movement profile of the patient over a long period of time, for example, over 24 hours or more, in order to be able to draw conclusions about his typical movements or activities.

To establish a movement profile, movement sensors, such as acceleration sensors, are typically attached to the body of the patient, for example, on a belt. It may be established via the sensors whether the patient stands, walks, or runs. A corresponding activity profile may be established over the day and optionally the night on the basis of these data. In order to be able to optimally detect the various activities, i.e., for example, standing or walking, cycling, swimming, or jogging, the sensor is typically fastened on various body positions, e.g., on the hip, on the foot, on the thigh, on the lower leg, on the chest, or on the arm. To be able to evaluate the various movement signals from the various body positions correctly, it is necessary to interpret the sensor signals, i.e., for example, the acceleration signals, differently depending on the particular position. For this purpose, it may be necessary to use various algorithms to analyze the signals or to employ various operating modes of the sensor or of a data processing unit. Thus, for example, in the case of triathlon watches, upon a change from running to cycling, the mode of an activity-detecting watch is manually changed over in order to be able to correctly establish the step count during running or the cadence during cycling. In the case of other applications, it is necessary to change the position of the movement sensor on the body during different activities, i.e., the sensor is initially worn on the hip and later on the lower leg, for example. A changeover of the operating mode is also necessary.

However, a changeover or a change of the operating mode is primarily problematic in the field of medicine and primarily represents an impediment in the case of older patients or patients who are restricted in any way. This may be because the particular patient is possibly not technically adept. The operation of a button or the operating selection via a menu may be difficult in the case of small buttons or a small display screen, in particular if the patient is restricted with respect to motor skills or vision. Above all, a changeover of the operating mode requires a certain attentiveness and concentration, which may not always be expected in particular in the case of longer-term establishment of a movement profile over multiple hours or over an entire day, so that deficient operation of corresponding sensors and therefore incorrect interpretation and classification of the sensor signals easily occur. Of course, such incorrectly established movement profiles are not very meaningful.

SUMMARY

An object of the present is to make it easier to establish a movement profile of a human and to eliminate possible error sources. This object may be achieved by an example movement sensor, use of such a sensor, and an example system for establishing a movement profile of a living being, in particular a human, in accordance with the present invention.

An example movement sensor according to the present invention is provided for establishing a movement profile of a living being, in particular a human, and is characterized in that it has an element or elements for automatically changing between various operating modes. For this purpose, for example, an algorithm for analyzing the data within the scope of another operating mode may be changed over. The elements for automatic change may be switching units or programmable control units, for example, which are assigned to the movement sensor. Through the automatic change of the operating modes, it is possible to analyze the established movement data locally in the movement sensor.

The various operating modes relate to the fact that different movement patterns may be established at various positions of the movement sensor on the body of the living being, so that the sensor detects different movement signals, for example, acceleration signals, depending on the position on the body.

It is particularly preferably provided that the change between the various operating modes takes place as a function of an identifier of a fastening element, which may be electronically analyzed in particular, which is provided for an attachment to a specific point of the body of the living being, in particular the human, so that through the particular identifier of the specific fastening element, the sensor may read out the data and may thus infer its position on the body.

In one particularly preferred specific embodiment of the movement sensor according to the present invention, an automatic change between various operating modes is provided, the particular operating mode relating to different environmental conditions. The various operating modes are preferably an operating mode for movements in the air and an operating mode for movements in water. This means that by changing over these operating modes, it is possible to differentiate between a movement in air and a movement in water, i.e., in particular swimming. The corresponding movement or acceleration signals are analyzed in accordance with a movement in air, i.e., in particular walking, standing, sitting, lying down, etc., and a movement in water, i.e., in particular swimming. Exercises in water play a large role within the scope of medical rehabilitation. For many patients, in particular also the chronically ill or older persons, a movement in water represents a very suitable form of movement in order to be physically active. The movement sensor according to the present invention is suitable in a particularly advantageous way for detecting the activity in the water and for taking the activity in water into consideration within the scope of a longer-term movement profile. In this case, the acceleration sensor may differentiate between different environmental conditions, i.e., in particular between air and water, so that the acceleration sensor may automatically select the particular suitable operating mode or accordingly change to the operating mode. Without a change of the operating mode from air to water, an activity during swimming would be incorrectly interpreted, for example, a backstroke would be interpreted as lying down. It is therefore provided according to the present invention that a change into the water is detected by the movement sensor and thus another analysis and interpretation of the detected movement signals may take place. The particular advantage of the present invention is that this changeover takes place automatically, without the operator or user having to think about it. In this way, possible incorrect inputs during the operation of the sensor or the corresponding device are also prevented beforehand. A change between an activity in the water and an activity in the air is therefore detectable without intervention of the user, so that a very detailed movement log may be established in a simple way.

In one particularly preferred specific embodiment of the movement sensor according to the present invention, it is provided that an additional sensor for detecting the changing environmental conditions is assigned to the movement sensor. In particular, water may be differentiated from air by the additional sensor. For example, a sensor for detecting the moisture, the temperature, the pressure, and/or the resistance is particularly preferably provided as the additional sensor. For example, a capacitive moisture sensor may be used to detect the moisture. If this sensor detects moisture of a specific or predefinable degree, it may be concluded that the sensor and therefore the person is located in water. Another option is a temperature sensor as an additional sensor. The water temperature typically differs from the air temperature, so that upon the detection of a sudden temperature change, it may be concluded that the person has changed from the air into the water. Typical water temperatures, as are to be encountered in the swimming pool, for example, may be taken into consideration for this purpose, so that incorrect interpretations do not occur when the person changes from an interior to the outside, for example. Here also, a sudden temperature change may occur. Furthermore, a pressure sensor may be used as an additional sensor, for example, since different pressure conditions prevail in the water than outside the water. Another option is the measurement of the resistance, in particular the transition resistance between two contacts, for example, between the contacts of a charging plug. The resistance between two contacts depends on the ambient medium, and therefore the transition resistance changes between two contacts when a change takes place between water and air. By monitoring the resistance, it may therefore be detected whether the movement sensor is in the water or in the air. The use of the resistance measurement between two contacts has the particular advantage that such contacts are typically present in any case, in particular if the movement sensor is operated via batteries, so that no further components are necessary for the additional sensor for detecting air or water. If the movement sensor is operated via batteries, contacts are typically led outward in order to charge the battery. These contacts are generally monitored in that it is checked whether a charging current is present, for example. In this way it may be detected whether the movement sensor is in a charging station. Only a slight modification of the sensor, e.g., an additional terminal on an A/D converter, is necessary to monitor the transition resistance between these contacts with respect to a detection of the environmental conditions. The following states may thus be detected on the basis of these contacts:

- sensor in the charging station (e.g., charging current present and additionally a "short-circuit" of the contacts through the voltage source)
- sensor in the air (high internal resistance between the contacts)
- sensor in the water (low internal resistance between the contacts).

In this specific embodiment, it is possible without special effort, in addition to establishing the movement profile through the movement sensor, to establish whether the movement sensor is located in the water or in the air, so that the corresponding operating mode may be set automatically without user intervention.

If additional sensors are used to detect moisture, temperature, and/or pressure with respect to the detection of air in contrast to water, for example, these sensors may also be used in another way. For example, a pressure sensor may be used to detect meters in altitude when climbing stairs or when negotiating other grades. Furthermore, combinations of multiple additional sensors may be used in addition to the actual movement sensor, for example, a moisture sensor and the described sensory function for detecting the resistance, in order to increase the reliability of the movement sensor with respect to the automatic change of the operating modes.

In one particularly preferred specific embodiment, an acceleration sensor, in particular a three-axis acceleration sensor, is used as the movement sensor, which, in addition to the detection of a detailed movement pattern based on the Earth's gravitational pull, may also detect the geometrical orientation of the sensor or the orientation of the sensor in the gravitational field of the Earth. In one particularly preferred specific embodiment of the movement sensor according to the present invention, the orientation of the person in the gravitational field of the Earth may be inferred by its position on the body of the person or the living being, so that the position of the person may be established. For example, if the movement sensor is fastened on the hip or on the thigh of a person in a defined orientation or positioning, it may be concluded whether the person is lying down or standing. Through the additional information as to whether the person is located in the water or in the air, in the case of a horizontal position, it may be concluded whether the person is lying down or swimming. Furthermore, an acceleration sensor detects the movement of the person, so that, for example, in the case of a recumbent position in the water, the number of the swimming strokes may be counted on the basis of the leg movements.

Furthermore, the present invention includes a system for establishing a movement profile of a living being, in particular a human. The system includes at least one movement sensor and at least one, preferably two or more, fastening elements for fastening the movement sensor on the living being or human. The fastening element may be, for example, a belt, a strap, a wristband, or a leg strap. The system according to the present invention is primarily characterized in that the fastening element has an element for an identifier, which may be electronically analyzed in particular by the movement sensor. This system allows the movement sensor to be fastened via a specific fastening element on the body of the person or the patient and allows the position of the movement sensor fastened on the body to be detected with the aid of the identifier, which is specific to the particular fastening element and therefore specific to the position on the body of the person, and therefore may be taken into consideration during the analysis of established data of the movement sensor. For example, if the sensor is attached to a belt, which is applied around the waist of the patient, it may be detected by the sensor on the basis of the specific identifier of the belt that the sensor is located on the waist. For example, if the sensor is removed from the belt and fastened to a wristband having an appropriate identifier, the sensor in turn detects the position on the arm of the patient, so that this information may be taken into consideration automatically during the analysis and interpretation of received movement signals of the sensor.

Thus, the sensor may be fastened to a specific position of the body depending on the need and intended activity of the person. An optimum fastening position for everyday movements, i.e., in particular sitting, standing, lying down, and walking, is a fastening on a belt for the hip or waist, for example. An optimum position of the sensor for swimming is the thigh. An optimum position for the sensor during cycling is the lower leg. An optimum position for running or jogging is the foot. Various holders or fastening elements are preferably used for fastening the sensor to the various body positions. For example, the sensor may be plugged into a clip which may be fastened on the shoelaces for an attachment on the foot. Rubber bands or straps of different lengths may be used for the lower leg and the thigh. A rubber band or strap of specific length is also usable for an attachment to the chest, for example. A belt or a belt clip may be used for an attachment to the hip.

According to the present invention, the various fastening elements, using which the sensor is fastened on the body, are detected automatically or with the aid of an appropriate identifier element. The fastening position is inferred from this detection, so that a suitable interpretation and analysis or a suitable operating mode may be set automatically, without an interaction of the user with the device or a user input being required. In this way, errors during the operation of the device or the sensor or an unintentional omission of the operation or the input on the device are avoided, so that incorrect analysis and interpretation of the data of the movement sensor do not occur. The system according to the present invention is therefore suitable in particular for establishing movement profiles in the field of medicine, in which incorrect operation or incorrect interpretation of data may have particularly wide-ranging and disadvantageous consequences for the patient. The system according to the present invention is further characterized in that an arrangement is provided for automatically changing between various operating modes of the movement sensor as a function of the identifier, the various operating modes being based on different movement patterns at different positions of the movement sensor on the body of the living being. Depending on the position of the sensor on the body of the living being, the movement sensor detects different movements; thus, for example, hardly any activity is to be detected on the arms during cycling, while in contrast the movements detectable on the lower leg are greatest. These different movement patterns as a function of the particular movement activity are taken into consideration according to the present invention in that the different movement patterns during various activities are the foundation of the various operating modes of the movement sensor, so that the data analysis is adapted to the various movement patterns during the various movement activities.

A movement profile may be established in such a way that, for example, the duration of the various activities, i.e., for example, sitting, lying down, standing, walking, cycling, etc., is established. Furthermore; for example, the number of steps or the step frequency during walking or running or the cadence during cycling may be established. Both may be combined with one another and documented as the course of a day of the movement activities, for example.

It is possible according to the present invention to use only one movement sensor for the preparation or establishment of the movement profile, which may optimally detect the various physical activities depending on its position on the body. On the one hand, this increases the wearing comfort for the user; on the other hand, the costs for the system are decreased due to this reduction of the number of the sensors. In certain circumstances, it may be advantageous to use more than one sensor in the system according to the present invention, in order to make the operation easier for the user in particular. This may be advantageous, for example, if a sensor is to be attached to a position on the body which is difficult to access for the patient himself, for example, on the back. In such cases, it may be provided that one sensor is fastened on the back and an additional sensor is provided for alternating use on all other positions on the body, for example, on the ankle, on the thigh, on the hip, and on the arm.

A conventional acceleration sensor is preferably used as the movement sensor, in particular a three-axis acceleration sensor, which may detect an acceleration in the direction of the three axes of a Cartesian coordinate system. More detailed movement patterns may thus be detected. Using such an acceleration sensor, for example, the foot movement may be observed and the number of steps may be counted, the leg or arm movements during swimming may be observed, and accordingly the swimming strokes may be counted, or the leg movement may be observed during cycling and accordingly the revolutions may be counted in a particularly advantageous way depending on the attachment of the sensor. Furthermore, using an acceleration sensor, the geometrical orientation of the sensor may be determined based on the detected Earth's gravitational pull, so that the orientation of the sensor in the gravitational field of the Earth may be determined. This has the advantage that with defined positioning of the sensor on the body of the person or the living being, the position of the person, i.e., for example, standing or lying down, or the position of the limb, to which the sensor is fastened, may be detected.

For the automatic detection according to the present invention of the fastening element by the movement sensor, the fastening element is coded in such a way that the fastening sensor may read out the code and therefore the type of the fastening element and its provided position on the body. For example, an analog code, a magnetic code, a mechanical code, and/or radio frequency-based communication element are suitable as the element for the identifier of the fastening element. For example, a chip having a stored identifier may be integrated into the fastening element. A code based on a contact-based communication, for example, a so-called iButton (1-wire® RFID alternative) or a near field communication (NFC), which is based on the RFID system, is suitable, for example. A resistance between two measuring points may be established as an analog code, for example. In the case of a magnetic code, for example, a field strength induced by the means for the identifier is incorporated. A mechanical code is possible in a binary way by short-circuiting different contacts, for example.

The power supply of the element for the identifier may take place with the aid of a battery, for example. The element for the identifier is particularly advantageously not equipped with a separate power supply, however, in order to be able to design the fastening element having the means for the identifier as very simple and robust. A separate power supply on the fastening element requires additional contacts for the power supply, which increase the complexity and therefore possibly make it more difficult to handle. The identifier is therefore particularly advantageously externally supplied with power.

In a preferred embodiment of the system according to the present invention, the at least one fastening element and/or the movement sensor is/are equipped with a mechanical element for fastening the movement sensor. Clips, guide rails, pockets, hook-and-loop closures, and/or snap fasteners are particularly advantageously used for this purpose. In particular, a use of guide rails or the use of snap fasteners for fastening the sensor on the fastening element allows a particularly secure hold with simple operation and good contact possibilities for the sensor. For example, an iButton may be integrated into a snap fastener part of the fastening element, which is read out when the sensor is attached, which has the corresponding counterpart of the snap fastener. In other specific embodiments, the fastening element includes a pocket, into which the sensor is inserted in a predefined direction, the pocket having a chip, for example, which is read out by the sensor.

It is provided according to the present invention that any type of fastening, i.e., for example, a belt, a tie strap for the lower leg, a tie strap for the thigh, a tie strap for the arm, a chest strap, etc., receives an individual identifier, which is read out or detected in each case by the fastening sensor and thus allows an automatic activation of the corresponding operating mode of the sensor, which takes into consideration the specific movement pattern at the corresponding position of the body for a specific activity and causes a corresponding data analysis. In this case, it is provided in a preferred embodiment of the present invention that the user of the movement sensor changes the position of the sensor on the body as a function of the particular intended movement activity, i.e., for example, carries the sensor on the belt during everyday movement such as walking, standing, or running, and disconnects the sensor from the belt and attaches it to a corresponding fastening element on the lower leg in preparation for cycling. A further interaction with the sensor is not necessary, since the sensor detects the particular position on the body and independently and automatically sets a different operating mode adapted to the new type of movement.

Furthermore, the present invention includes the use of a movement sensor, in particular an acceleration sensor, for establishing a movement profile of a living being, for example, a person, the movement sensor automatically changing between various operating modes. The change of the operating modes takes place preferably as a function of the position of the movement sensor on the body of the living being, the position of the movement sensor being determined with the aid of an identifier, which may be electronically analyzed in particular, of a fastening element for the movement sensor on the body of the living being. The change of the various operating modes takes place preferably as a function of different environmental conditions, the various operating modes including a mode for movements in air and a mode for movements in water, for example. At least one additional sensor for differentiating between the various environmental conditions is preferably assigned to the movement sensor for this purpose.

Finally, the present invention includes the use of a movement sensor for detecting an essentially upright position or an essentially horizontal position, in particular a standing or recumbent position of the person or the living being, the movement sensor being attached in a defined position or orientation on the body of the living being and the detection of the standing or recumbent position or a vertical or horizontal orientation taking place by detecting the Earth's acceleration by the movement sensor, preferably an acceleration sensor. Reference is made to the above-mentioned description with respect to additional features of the example movement sensor according to the present invention.

Further advantages and features of the present invention are described below in the context of exemplary embodiments and in connection with the figures. The various features may each be implemented alone or in combination with one another for this purpose.

DETAILED DESCRIPTION OF EXAMPLE EMBODIMENTS

Figure 1:
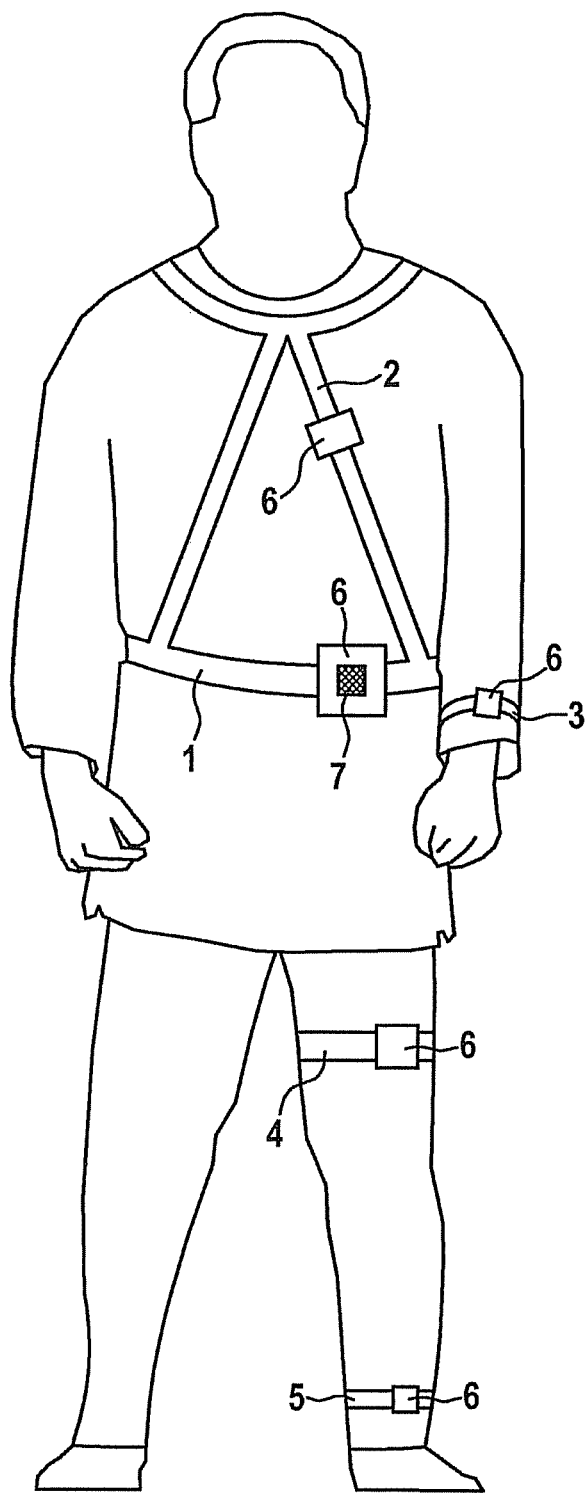
FIG. 1 shows a schematic view of a person having various fastening elements for an example movement sensor according to a preferred embodiment of the system according to the present invention.

The person shown in FIG. 1 carries multiple fastening elements in the form of a hip strap 1, a chest strap 2, a wristband 3, a thigh strap 4, and a lower leg or foot strap 5. These fastening elements each have a device 6 for fastening a movement sensor. These may be clips, snap fasteners, guide rails, pockets, or comparable elements, for example. Devices 6 of fastening straps 1, 2, 3, 4, and 5 are equipped with an identifier, which may be electronically analyzed by movement sensor 7. In this example, movement sensor 7 is fastened on fastening device 6 of hip strap 1. Through the individual identifier of the fastening device on hip strap 1, movement sensor 7 may electronically read out this identifier and therefore infer its position on the body of the person, in this case the position in the middle of the body or on the hip of the person. Since the various body parts are subject to different movement patterns during various physical activities of the person, the signals detected by the movement sensor may be analyzed differently depending on the position on the body within the scope of different operating modes. It is preferably provided that the person changes the position of sensor 7 in the event of a change of his activity, i.e., for example, when he changes from walking to cycling, in that he removes sensor 7 from hip strap 1 and fastens it on foot strap 5. Through the individual identifier of particular fastening element 1 or 5, sensor 7 detects its position on the body of the person and automatically sets the particular suitable operating mode, so that the person himself does not have to perform any type of input on sensor 7.

In a preferred specific embodiment of the system according to the present invention, it may be provided that a "default" mode is provided, which is executed when no identifier is detected by the movement sensor. For example, a "normal" position on hip strap 1 may be presumed. This position of movement sensor 7 is used for everyday movements, i.e., walking, standing, lying down, etc. The hip strap is not equipped with an identifier in this specific embodiment, so that the sensor concludes this starting position when it cannot detect an identifier. As soon as the sensor cannot detect an identifier, it thus presumes that it is worn on the hip and switches into the corresponding operating mode. In this specific embodiment, the expenditure may thus be reduced for the system according to the present invention by dispensing with the means for identification on the hip strap.

Alternatively thereto, the movement sensor may be put into a sleep mode when it cannot detect an identifier. In this case, it is presumed that the movement sensor is not worn or is worn on the body in a pocket independently of a fastening element, for example. As long as no fastening element is detected, it is not necessary to read out and analyze the movement signals. The sleep mode is preferably coupled with a low energy consumption. In this mode, it is detected only when the movement sensor is fastened on a fastening element in order to reactivate itself.

Figure 2:
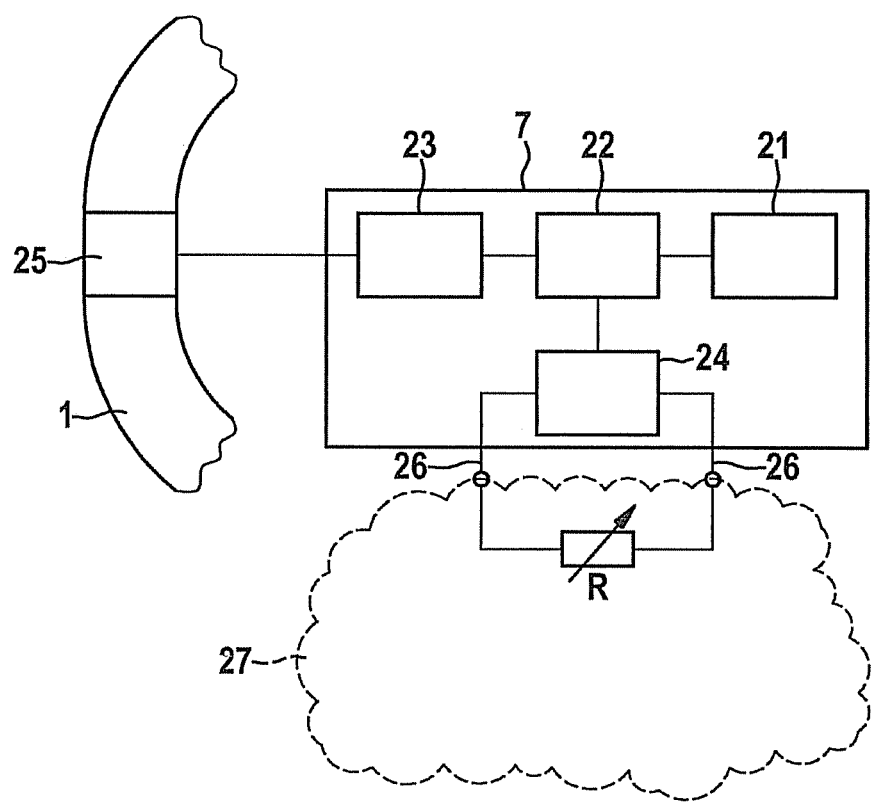
FIG. 2 shows a schematic view of an example movement sensor according to the present invention.

FIG. 2 illustrates an example movement sensor according to the present invention. Movement sensor 7 includes actual movement sensor unit 21, for example, an acceleration sensor, a unit 22 for automatically changing between various operating modes, a unit 23 for detecting the sensor position on the body, and an additional sensor 24, which is provided for detecting moisture. When movement sensor 7 is attached to a fastening element 1, movement sensor 7 detects the position of the movement sensor on the body with the aid of unit 23 on the basis of an identifier 25 on fastening element 1, which is specific to fastening element 1 or its position on the body. Sensor 24 detects the moisture of schematically indicated surroundings 27 of movement sensor 7 via a measurement of transition resistance R between two contacts 26. Resistance R between contacts 26 depends on the ambient medium, so that the transition resistance changes when a change is carried out between water and air, for example. By monitoring the resistance, it may therefore be detected whether environmental conditions 27 change, i.e., for example, whether a change has occurred from the air into the water. With the aid of this information obtained by additional sensor means 24 and the information about the position of movement sensor 7 on the body obtained with the aid of unit 23, the corresponding mode selection take place with the aid of unit 22, so that the data of actual movement sensor 21 may be analyzed appropriately. Both the operating mode defined at the outset, which is based on different movement patterns at different positions of the movement sensor on the body of the patient, and the operating mode defined at the outset, which considers the various environmental conditions, i.e., in particular water and air, are incorporated in the mode selection in this case.

What is claimed is:

1. A movement sensor system for establishing a movement profile of a human, comprising:
    a movement sensor unit;
    an at least one additional sensor unit to detect different environmental conditions; and
    a control unit for automatically changing between various operating modes of the movement sensor unit as a function of the different environmental conditions provided by the at least one additional sensor unit, in order to determine the movement profile.

2. The system as recited in claim 1, wherein the movement profile represents analysis of a physical activity including at least one of sitting, lying down, standing, walking, cycling, swimming, and running.

3. The system as recited in claim 1, wherein the various operating modes each implements a different set of algorithms.

4. The system as recited in claim 1, wherein the at least one additional sensor unit comprises a device measuring a resistance between a first contact and a second contact, wherein the resistance is used to determine whether the movement sensor system is in water.

5. The system as recited in claim 1, wherein the at least one additional sensor unit comprises a capacitive moisture sensor.

6. The movement sensor system as recited in claim 1 wherein the automatically changing between various operating modes of the movement sensor unit is provided as a function of an identifier of at least one fastening element which is analyzed by the movement sensor, the various operating modes being based on different movement patterns at different positions of the movement sensor on a body of the human.

7. The system as recited in claim 1, wherein the various operating modes include a mode for movements in air and a mode for movements in water.

8. The system as recited in claim 1, wherein the environmental conditions include at least one of moisture, temperature, pressure, and resistance.

9. The movement sensor system as recited in claim 1, wherein the movement sensor unit is provided for defined positioning on the body of the living being.

10. A method for establishing a movement profile of a human, comprising:
    detecting by a sensor unit at least one of a plurality of different environmental conditions; and
    determining the movement profile by automatically changing between various operating modes of a movement sensor unit as a function of at least one of the detected different environmental conditions.

11. The method as recited in claim 10, wherein the automatically changing between various operating modes of the movement sensor takes place as a function of a position of the movement sensor on a body of the human, the position of the movement sensor on the body of the human being determined using an identifier of at least one fastening element, which is analyzed by the movement sensor.

* * * * *